(12) United States Patent
Schmitz et al.

(10) Patent No.: US 9,259,506 B2
(45) Date of Patent: Feb. 16, 2016

(54) HYDROGELLING FIBERS AND FIBROUS STRUCTURES

(71) Applicant: Carl Freudenberg KG, Weinheim (DE)

(72) Inventors: Wiebke Schmitz, Gauting (DE); Bernd Schlesselmann, Weinheim (DE); Katharina Krampfl, Viernheim (DE); Marc Pehr, Heppenheim (DE)

(73) Assignee: CARL FREUDENBERG KG, Weinheim (DE)

( * ) Notice: Subject to any disclaimer, the term of this patent is extended or adjusted under 35 U.S.C. 154(b) by 406 days.

(21) Appl. No.: 13/856,481

(22) Filed: Apr. 4, 2013

(65) Prior Publication Data

US 2013/0274415 A1 Oct. 17, 2013

(30) Foreign Application Priority Data

Apr. 13, 2012 (DE) .......................... 10 2012 007 307

(51) Int. Cl.
*C08F 16/06* (2006.01)
*C08G 63/48* (2006.01)
(Continued)

(52) U.S. Cl.
CPC ............. *A61L 26/0014* (2013.01); *A61L 15/24* (2013.01); *A61L 17/10* (2013.01); *A61L 26/0052* (2013.01); *A61L 27/16* (2013.01); *D01D 10/02* (2013.01); *D01F 6/14* (2013.01); *D01F 6/50* (2013.01)

(58) Field of Classification Search
CPC ..... A61L 26/0052; A61L 27/16; A61L 15/24; A61L 17/10; A61L 26/0014; D01D 10/02; D01F 6/14; D01F 6/50; C08L 29/04

USPC ................ 525/58, 56; 526/317.1, 319, 238.3, 526/303.1, 238.2
See application file for complete search history.

(56) References Cited

U.S. PATENT DOCUMENTS 5,717,026 A 2/1998 Ikimine et al.
6,139,963 A 10/2000 Fujii et al.
(Continued)

FOREIGN PATENT DOCUMENTS

CN 103154347 A 6/2013
DE 69609770 T2 4/2001
(Continued)

OTHER PUBLICATIONS

Lei Li et al.: "Ultra-Fine Polyelectrolyte Hydrogel Fibres From Polyacrlic Acid/Poly(Vinyl Alchohol)", Nanotechnology, vol. 16, No. 12, Dec. 1, 2005, pp. 2852-2860.*
(Continued)

*Primary Examiner* — William Cheung
(74) *Attorney, Agent, or Firm* — Leydig, Voit & Mayer, Ltd.

(57) ABSTRACT

Fibers or one-dimensional, two-dimensional, or three-dimensional fibrous structures configured to be hydrogelling, produced from fibers made of a first fiber raw material, whereby the first fiber raw material contains water-soluble polyvinyl alcohol and/or polyvinyl alcohol copolymer, whereby the hydrogelling configuration of the fibers or fibrous structures is achieved by tempering the fiber raw material at a predetermined tempering temperature that is preferably higher than the glass transition temperature and/or lower than the melting or decomposition temperature of the first fiber raw material employed, as well as by tempering for a predetermined tempering duration, and whereby the fiber raw material is cross-linked by the tempering.

20 Claims, 1 Drawing Sheet

(51) Int. Cl.

| | |
|---|---|
| *C08B 37/00* | (2006.01) |
| *C09D 11/10* | (2014.01) |
| *C08F 20/00* | (2006.01) |
| *C08F 20/06* | (2006.01) |
| *C08F 118/02* | (2006.01) |
| *A61L 26/00* | (2006.01) |
| *A61L 27/16* | (2006.01) |
| *A61L 15/24* | (2006.01) |
| *A61L 17/10* | (2006.01) |
| *D01D 10/02* | (2006.01) |
| *D01F 6/14* | (2006.01) |
| *D01F 6/50* | (2006.01) |

(56) References Cited

U.S. PATENT DOCUMENTS

| | | |
|---|---|---|
| 2004/0105880 A1 | 6/2004 | Turner et al. |
| 2008/0112984 A1 | 5/2008 | Schulte et al. |
| 2010/0285101 A1 | 11/2010 | Moore et al. |
| 2013/0323195 A1 | 12/2013 | Schmitz et al. |

FOREIGN PATENT DOCUMENTS

| | | |
|---|---|---|
| DE | 69721454 T2 | 2/2004 |
| DE | 10 2010 048 407 A1 | 4/2012 |
| EP | 0745708 A2 | 12/1996 |
| WO | 01/30407 A1 | 5/2001 |
| WO | 2005103097 A1 | 11/2005 |
| WO | 2009085679 A1 | 7/2009 |
| WO | 2012048768 A1 | 4/2012 |

OTHER PUBLICATIONS

Jianqi F et al,: "PVA/PAA Thermo Crosslining Hydrogel Fiber: Preparation and PH-Sensitive Properties in Eletrolyte Solution" European Polymer Journal, vol. 38, No. 8, Aug. 1, 2002, pp. 1653-1658

Lei Li et al: "Ultra-Fine Polyelectrolyte Hydrogel Fibres From Polyacrlic Acid . . . " Nanotechnology vol. 16, No. 12, Dec. 1, 2005, pp. 2852-2860.

Ahmet Cay et al. "Properties of Elecetrospun Polvinyl Alcohol Hydrogel Nanofibers Crosslinked with . . . " Journal of Applied Polymer Science, vol. 129, No. 6, Feb. 18, 2013, pp. 3140-3149.

* cited by examiner

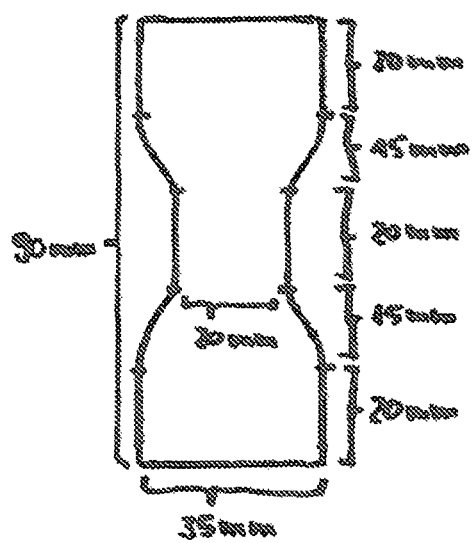

HYDROGELLING FIBERS AND FIBROUS STRUCTURES

CROSS-REFERENCE TO RELATED APPLICATIONS

Priority is claimed to German Patent Application No. 10 2012 007 307.0, filed on Apr. 13, 2012, the entire disclosure of which is hereby incorporated by reference herein.

FIELD

The present invention relates to hydrogelling fibers or one-dimensional, two-dimensional or three-dimensional fibrous structures that are made of a first fiber raw material, whereby the first fiber raw material contains water-soluble polyvinyl alcohol and/or polyvinyl alcohol copolymer as well as to an associated production method. Moreover, the invention relates to the use of such fibers or fibrous structures for wound care, especially in products for medical care such as wound dressings, as well as in hygiene and cosmetic products or the like. The invention also relates to products for medical care, especially wound dressings, as well as hygiene and cosmetic products.

The fibers or fibrous structures according to the invention can be advantageously used in direct contact with the wound or the body. Products for wound care made of the fibers or fibrous structures according to the invention swell upon contact with aqueous solutions or wound exudate and form a stable hydrogel that has an exceptionally high maximum breaking force and maximum breaking elongation. As a result, wound dressings containing the fibers or fibrous structures according to the invention can be removed from the wound in one piece. Moreover, the fibers or fibrous structures according to the invention have a particularly high absorption capacity as well as a particularly high retention capacity for aqueous solutions.

BACKGROUND

International patent application WO 01/30407 A1 describes a method for the production of hydrogels for use as wound dressings with which burns or other skin injuries can be treated. Within the scope of the method, an aqueous solution of polyvinyl alcohol, agar-agar and at least another natural polymer is prepared. This solution is filled into disposable plastic containers at 70° C. to 80° C. and sealed. After having cooled off to room temperature, the samples that had been filled into the disposable plastic containers are irradiated and thus sterilized.

International patent application WO 2005/103097 A1 describes hydrogels that have at least one polyvinyl alcohol star polymer. Here, the hydrogels are produced by repeatedly freezing and thawing an aqueous solution containing at least one polyvinyl alcohol star polymer and optionally additional components. Moreover, such hydrogels can be produced through the action of ionizing radiation of an aqueous solution containing at least one polyvinyl alcohol star polymer or by reacting a polyvinyl alcohol star polymer in an aqueous solution with cross-linking reagents.

A drawback of the currently known methods for the production of hydrogels, especially for treating wounds, is the laborious production method and the problematic further processing of the hydrogels as well as, if applicable, the occurrence of chemical impurities in the hydrogels that have been cross-linked, for instance, by means of a chemical reaction. Moreover, hydrogel films, in contrast to fibers and fibrous structures, have a smaller surface area, as a result of which they have less absorption capacity for water or aqueous solutions. Especially when polyvinyl alcohol is used as the raw material for hydrogels, care must be taken to ensure that the polyvinyl alcohol has a high degree of cross-linking since otherwise, no hydrogels are formed but instead, solutions of the polyvinyl alcohol in the liquid medium. Consequently, a high stability of the polyvinyl alcohol vis-à-vis water or aqueous solutions is desirable. Moreover, it is precisely polyvinyl alcohol and polyvinyl alcohol copolymers that stand out for their high biocompatibility and biotolerability, so that there is a rising demand for further variants of hydrogels or hydrogelling materials containing polyvinyl alcohol and/or polyvinyl alcohol copolymers that can also be produced cost-effectively and easily, while allowing unproblematic further processing.

J. Mater. Sci. (2010) 45:2456-2465 describes a method for the production of nanofibers and fibrous structures made of polyvinyl alcohol by means of electrospinning, in which the fibers or fibrous structures are stabilized vis-à-vis aqueous solutions by means of a temperature treatment. A drawback of fibrous structures made of nanofibers is that, due to their fiber diameter, which is between 244 nm and 270 nm, they exhibit a very low strength and maximum breaking elongation as well as only a low absorption capacity. Furthermore, the described fibers are stabilized vis-à-vis aqueous solutions so that they have no gelling properties, do not swell in aqueous solutions and are not suitable to trap water in the fiber (lack of retention capacity).

Wound dressings made of hydrogelling fibers, for example, of carboxymethyl cellulose or modified cellulose, are fundamentally known. However, they form a very soft hydrogel with a low maximum breaking force and maximum breaking elongation upon contact with the wound fluid. The drawback here is that they are difficult to remove in one piece from the wound or from the wound cavity. Thus, it can happen that residues of the wound dressing are left behind in the wound, and these then have to be removed by means of laborious cleaning of the wound. This takes more time for the hospital personnel and thus also involves more costs. Moreover, the would can be damaged or injured again by the cleaning procedure.

Fibers made of polyvinyl alcohol are commercially available in various types and they include polyvinyl alcohol having different levels of water solubility. Water-insoluble types of polyvinyl alcohol are, for example, the so-called high-strength polyvinyl alcohol fibers having a particularly high maximum breaking force in the dry state. Commercially available water-soluble fibers made of polyvinyl alcohol can be obtained with a temperature-dependent water solubility, for example, a water solubility above a temperature of 90° C., 70° C., 60° C., 40° C. or 20° C. Commercially available fibers made of polyvinyl alcohol can vary in terms of their water solubility, but they have no hydrogelling properties and thus display no retention capacity for water either.

SUMMARY

An aspect of the invention provides a plurality of fibers, configured to be hydrogelling, produced from fibers made of a first fiber raw material comprising water-soluble polyvinyl alcohol, polyvinyl alcohol copolymer, or water-soluble polyvinyl alcohol and polyvinyl alcohol copolymer, wherein a hydrogelling configuration of the plurality is achieved by (i) tempering a fiber raw material at a predetermined tempering temperature that is higher than a glass transition temperature, lower than a melting or decomposition temperature, or higher than the glass transition temperature and lower than the melting or decomposition temperature of the first fiber raw material, and (ii) tempering for a predetermined tempering duration, and wherein the fiber raw material is cross-linked by the tempering.

BRIEF DESCRIPTION OF THE DRAWINGS

FIG. 1 shows the stamping iron for stamping out the test specimens.

DETAILED DESCRIPTION

Therefore, the present invention has an objective of putting forward an improved embodiment pertaining to fibers or fibrous structures that are made of water-soluble polyvinyl alcohol, pertaining to their use, pertaining to an associated production method, and pertaining to wound bandages or wound dressings, said improved embodiments being characterized especially by simplified, cost-effective production and permitting an unproblematic further processing and/or use. Moreover, wound bandages or wound dressings made of the fibers or fibrous structures according to the invention are to have a greater stability, especially a high maximum breaking force and maximum breaking elongation in the hydrogelled state, so that they can be removed in one piece from the wound or from the wound cavity.

According to an object of the invention, this objective is achieved by the subject matters of the independent claims. Advantageous embodiments are the subject matter of the dependent claims.

Surprisingly, it was found that fibers or fibrous structures containing water-soluble polyvinyl alcohol can be treated by tempering in such a way that they form a stable hydrogel upon contact with aqueous solutions or wound exudates, especially with a 0.9% aqueous solution of sodium chloride (physiological saline solution) or with an aqueous solution according to the Test Solution A cited in DIN 13726-1 under Point 3.2.2.3, and this hydrogel has a very high maximum breaking force and maximum breaking elongation. Moreover, such fibers or fibrous structures have a high stability vis-à-vis water or aqueous solutions. Furthermore, the fibers or fibrous structures according to the invention are characterized by a high absorption capacity and a high retention capacity for water or aqueous solutions, especially for a 0.9% aqueous solution of sodium chloride (physiological saline solution) or an aqueous solution according to the Test Solution A cited in DIN 13726-1 under Point 3.2.2.3.

Therefore, in a first aspect of the invention, one-dimensional, two-dimensional or three-dimensional fibers or fibrous structures are proposed, which are produced from fibers made of a first fiber raw material, whereby the first fiber raw material contains water-soluble polyvinyl alcohol and/or polyvinyl alcohol copolymer, and whereby the fiber raw material is crosslinked for a predetermined tempering duration and configured to be hydrogelling in that it is tempered at a predetermined tempering temperature that is higher than the glass transition temperature and/or lower than the melting or decomposition temperature of the first fiber raw material employed. This treatment stabilizes the fiber raw material, and especially also the fibers or fibrous structures that are made of the fiber raw material, vis-à-vis aqueous solutions, so that these fibers or fibrous structures exhibit markedly reduced solubility in aqueous solutions. In this process, at the same time, the fibers or fibrous structures form a stable hydrogel upon contact with aqueous solutions.

Tempering as set forth in this invention refers to a process in which the fiber raw material, preferably in the form of fibers or fibrous structures, is heated at a predetermined temperature for a predetermined period of time, preferably at atmospheric pressure and in a gas atmosphere, especially air atmosphere. Advantageously, the fiber raw material in the form of fibers or a fibrous structure is tempered in the dry state, advantageously at a residual moisture of less than 10% by weight, even more preferably of less than 5% by weight, even more preferably of less than 3% by weight. Advantageously, the fibers or fibrous structures are first brought to the predetermined temperature and then kept for the predetermined period of time at this predetermined temperature. In this process, temperature fluctuations of at least ±10%, especially ±5% and preferably ±1% can be tolerated. Moreover, during the tempering process, any desired quantity of air can be fed in or withdrawn, and the air can be distributed in various ways (e.g. circulating air or continuous air) in the tempering zone. During the tempering process, other process gases such as nitrogen or oxygen can be additionally fed in so as to influence the tempering process and thus the properties of the fibers or fibrous structures in the desired manner.

Especially preferably, the tempering process is carried out with continuous air in a belt dryer in the case of the two-dimensional fibrous structures or nonwovens. In comparison to the tempering duration in the case of pure circulating air, the continuous air can reduce the tempering duration by several orders of magnitude.

Advantageously, the fibers or fibrous structures can be crosslinked by the tempering in such a way that they have a higher solubility stability vis-à-vis water. Moreover, due to the tempering, the fibers or fibrous structures acquire the capability to form a stable hydrogel upon contact with water or aqueous solutions, especially with a 0.9% aqueous solution of sodium chloride or with a solution according to the Test Solution A cited in DIN 13726-1 under Point 3.2.2.3, and this hydrogel is characterized by a very high maximum breaking force and maximum breaking elongation.

Moreover, the tempering can significantly reduce impurities or residues such as, for instance, spinning auxiliaries, brighteners, solvents or the like, or can even reduce them to a concentration below the applicable detection limit. Moreover, the fibers or fibrous structures according to the invention have a high absorption capacity and a high retention capacity for water, aqueous solutions, especially for a 0.9% aqueous solution of sodium chloride or for a solution according to the Test Solution A cited in DIN 13726-1 under Point 3.2.2.3 and/or for wound exudate.

Thus, the fibers or fibrous structures can have a retention capacity for water and/or aqueous solutions of more than 70%, preferably from 70% to 100%. In case of fibers and/or one-dimensional as well as two-dimensional fibrous structures, the relative retention capacity for a 0.9% aqueous solution of sodium chloride or for a solution according to the Test Solution A cited in DIN 13726-1 under Point 3.2.2.3 is over 70%, even more preferably over 80%, even more preferably 85%, even more preferably 85% to 100%.

Moreover, the fibers or fibrous structures can have a relative absorption capacity of 4 to 30 g/g for a 0.9% aqueous solution of sodium chloride or for a solution according to the Test Solution A cited in DIN 13726-1 under Point 3.2.2.3. In case of fibers and/or one-dimensional as well as two-dimensional fibrous structures, the relative absorption capacity for a 0.9% aqueous solution of sodium chloride or for a solution according to the Test Solution A cited in DIN 13726-1 under Point 3.2.2.3 is 4 to 30 g/g, especially preferably from 4 to 25 g/g, even more preferably from 5 to 20 g/g, even more preferably from 7 to 20 g/g. Thus, toxicologically safe and biocompatible fibers or fibrous structures as well as gels that can be mode from them, especially hydrogels, can advantageously be produced.

Consequently, the above-mentioned objective is achieved.

A fiber is defined as a structure that is thin and flexible relative to its length. Fibers have a small diameter and can be structured with each other by means of appropriate bonding techniques to form fibrous structures. Consequently, a fibrous structure can have multiple fibers. A distinction can be made between one-dimensional, two-dimensional and three-dimensional fibrous structures. A one-dimensional fibrous structure has a small width and a small height in comparison to its length. A two-dimensional fibrous structure has a small height in comparison to its length and width. Three-dimensional fibrous structures are defined as fibrous structures that have several layers of two-dimensional fibrous structures. Here, the individual layers of the three-dimensional fibrous structures can be joined together by means of the bonding techniques described below or in some other manner.

The dry or wet spinning methods can be used to produce filaments from polymers, and the spunbond method can be used to produce spunbond nonwovens. The filaments can be considered here as one-dimensional fibrous structures, whereas the spunbond nonwovens can be two-dimensional fibrous structures. By cutting and/or crimping the filaments, staple fibers can be produced that can be classified as one-dimensional fibrous structures. Yarn can be twisted to make staple fiber yarns from staple fibers. They can be considered as one-dimensional fibrous structures. Yarns structured from filaments can be made up of one filament (monofilament yarn) or of several filaments (multifilament yarn). They can likewise be considered as one-dimensional fibrous structures. Blended yarns can be produced by means of yarn-spinning of more than one different staple fiber or natural fiber. Yarns such as natural fiber yarns, staple fiber yarns or filament yarns or blended yarns can be further processed, for example, into wovens, knits, interlaid nonwovens or knit fabrics by means of textile processing techniques such as weaving, knitting, embroidering, laying or sewing. The wovens, knits and laid nonwovens can be considered as two-dimensional fibrous structures. Nonwoven techniques such as crimping or the air-laid method can make staple fiber nonwovens or air-laid nonwovens from staple fibers, and these nonwovens can likewise be considered as two-dimensional fibrous structures. According to the invention, preference is given to the use of water-soluble staple fibers that are laid to form a staple fiber nonwoven by means of crimping.

Unbonded nonwovens such as, for example, staple fiber nonwovens or spunbond nonwovens, can be bonded to form nonwovens. For example, calandering can be employed as the bonding method. In this process, the unbonded nonwovens are conveyed between rollers, whereby point seal surfaces on the rollers generate sealing points that at least partially penetrate the nonwovens. If punctiform sealing points are generated, then the bonding method is referred to as a PS (point-seal) bonding method. However, the formation of linear sealing points or full-surface sealing points is also possible. Another bonding method that can be used is hot-air bonding in a circulating air dryer, whereby this technique creates bonding through melted points at the contact points of the fibers. Moreover, the use of binders or binding agents is also conceivable, whereby here the fibers are joined to each other via bridges consisting of binders or binding agents. In particular, mechanical bonding techniques can also be employed such as, for example, the needle-punching method in which the bonding is performed by needles. Furthermore, fulling or felting or the like are also conceivable. Here, it is also possible to turn to a combination of several bonding techniques. Preferably, the needle-punching method and/or the PS bonding method are used.

The water-soluble fibers made of polyvinyl alcohol or the fibrous structures containing the water-soluble fibers made of polyvinyl alcohol can be crosslinked by means of the tempering procedure. Consequently, the fibers themselves as well as the fibrous structures can be changed by tempering in such a way that they acquire a greater stability vis-à-vis water, especially vis-à-vis a 0.9% aqueous solution of sodium chloride or vis-à-vis an aqueous solution according to the Test Solution A cited in DIN 13726-1 under Point 3.2.2.3.

The tempered fibers or else the fibrous structures made thereof preferably have a soluble content of 1% to 30%, preferably 1% to 25%, even more preferably 1% to 20% and even more preferably 1% to 15% in a 0.9% aqueous solution of sodium chloride or in an aqueous solution according to the Test Solution A cited in DIN 13726-1 under Point 3.2.2.3.

Moreover, the tempering gives the fibers or the fibrous structure the property of forming a stable hydrogel with a high maximum breaking force and maximum breaking elongation upon contact with water or with the above-mentioned solutions. The term "hydrogelling" refers to the capability to form a hydrogel that, as the liquid phase, has water or an aqueous solution, especially preferably a 0.9% aqueous solution of sodium chloride or an aqueous solution according to the Test Solution A cited in DIN 13726-1 under Point 3.2.2.3.

A hydrogel is a hydrophilic polymer network that has swelled in water. In particular, a hydrogel is a system consisting of at least one solid phase and one liquid phase, whereby the solid phase forms a three-dimensional network whose pores can be filled up by an aqueous solution, as a result of which they swell. Both phases can completely penetrate each other and consequently, a gel can store a liquid phase in a manner that is more stable vis-à-vis pressure than a sponge can. Moreover, a hydrogel has a high retention capacity for aqueous solutions.

Fibers or fibrous structures according to the invention are configured to be hydrogelling and consequently, they have an excellent binding and retention capacity for aqueous phases. They are preferably laid while still dry onto the wound or else wound cavities are filled with them. Together with the wound exudate, they form stable hydrogels, thus creating an optimal wound environment for wound healing without sticking to the wound. Such a moist wound treatment can assist the healing process. Due to the high maximum breaking force and maximum breaking elongation of the hydrogel formed with the wound exudate, the fibers or fibrous structures can be removed in one piece from the wound or from the wound cavity.

Likewise for moist wound treatment, the fibers or fibrous structures according to the invention can be used in hydrogelled form when provided with a liquid phase. Preferably, water is used here as the liquid phase, especially preferably a 0.9% aqueous solution of sodium chloride, a Ringer solution or solutions containing active ingredients, or a solution according to the Test Solution A cited in DIN 13726-1 under Point 3.2.2.3.

Polyvinyl alcohols are polymers and can be produced from polyvinyl acetate by means of hydrolysis. The technical properties of the polyvinyl alcohol such as especially its water solubility depend, among other things, on the production method, on the molar mass and on the remaining content of acetyl groups (degree of hydrolysis). As the molar mass and the degree of hydrolysis decrease, the solubility in water increases. Depending on the molar mass and on the degree of hydrolysis, the polyvinyl alcohols have a different water solubility. Thus, a few types of polyvinyl alcohol only dissolve in water at an elevated temperature (e.g. above 90° C.). Fibers made of polyvinyl alcohol are normally drawn to several times their original length during their production and, in this process, they can also be heated (drawing temperature) in order to increase the crystallinity and the strength of the fibers. In this context, the formation of intermolecular hydrogen bridges is made possible through the parallel orientation of the molecule chains. Thus, the water solubility of the polyvinyl alcohol fibers can also be selected.

According to the invention, the untempered fibers made of polyvinyl alcohol used as the first fiber raw material can already be water-soluble in an excess quantity of water below a temperature of 50° C., preferably below 40° C., especially preferably below 30° C., even more preferably below 25° C., whereby the untempered fibers can, of course, also be water-soluble above these values. Furthermore, the untempered fibers can also be water-soluble above 15° C. and/or above 20° C. In particular, the untempered fibers can be water-soluble in a range between 0° C. and 150° C., or between 5° C. and 100° C., or between 10° C. and 100° C., or between 15° C. and 100° C., or between 20° C. and 100° C., whereby the term water-soluble means that, in an excess quantity of water, the fibers dissolve by at least 70%, preferably by more than 80%, even more preferably by more than 90%, and especially by more than 95%, and especially by 100%.

The polyvinyl alcohol that is used for the production of the fibers made of polyvinyl alcohol can be modified by copolymerization with other monomers (e.g. polyethylene vinyl alcohol) or by incorporating functional groups, as a result of which additional physical as well as chemical properties can be systematically incorporated into the fibers, if applicable. Thus, if, for example, polyethylene vinyl alcohol is used, the number of OH groups is reduced.

Preferably, polyethylene vinyl alcohol, polyvinyl alcohol styrene, polyvinyl alcohol vinyl acetate, polyvinyl alcohol vinyl pyrrolidone, polyvinyl alcohol ethylene glycol and/or polyvinyl alcohol, especially preferably polyethylene vinyl alcohol, polyvinyl alcohol vinyl acetate, polyvinyl alcohol vinyl pyrrolidone, polyvinyl alcohol vinyl amine, polyvinyl alcohol acrylate, polyvinyl alcohol acrylamide, polyvinyl alcohol ethylene glycol can be used as polyvinyl alcohol copolymers. The polyvinyl alcohol copolymers can be present in the form of block copolymers and/or graft copolymers and/or block graft copolymers, statistical or alternating systems and any mixtures of these with each other. The content of other monomer units in the polyvinyl alcohol is 30% at the maximum, preferably 1% to 30%, even more preferably 5% to 15%, each relative to the total number of monomer units in the polyvinyl alcohol copolymer.

However, other functional groups can also be incorporated into the polyvinyl alcohol and/or into the fibers or fibrous structures, for example, by means of substitution or polymer-analog reactions. The options here as the functional groups are especially carboxylic acids, unsaturated carboxylic acids such as methyacrylic acids, acrylic acids, peroxycarboxylic acids, sulfonic acids, carboxylic acid esters, sulfonic acid esters, aldehydes, thioaldehydes, ketones, thioketones, amines, ethers, thioethers, isocyanates, thiocyanates, nitro-groups. The content of other functional groups in the polyvinyl alcohol is 30% at the maximum, preferably 1% to 30%, even more preferably 5% to 15%, each relative to the number of OH groups in the polyvinyl alcohol.

Moreover, the first fiber raw material can be configured as a physical mixture of the water-soluble polyvinyl alcohol and at least one other polymer (polymer blend). Here, the content of water-soluble polyvinyl alcohol in the polymer blend is at least 70% by weight, relative to the total weight of the polymer blend.

Advantageously, the resultant polymer blend has different physical properties and, if applicable, also different chemical properties as compared to the polymers employed. In this context, the properties of the polymer blend are normally a sum of the properties of the polymers employed. Thus, the use of polymer blends means that the selection of first fiber raw materials can be further expanded.

Here, in order to make such a polymer blend, additional gelling polymers can be used such as, for example, alginates, cellulose ethers such as carboxymethyl celluloses, methyl celluloses, ethyl celluloses, hydroxymethyl celluloses, hydroxyethyl celluloses, hydroxyalkylmethyl celluloses, hydroxypropyl celluloses, cellulose esters such as cellulose acetate, oxidized celluloses, bacterial celluloses, cellulose carbonates, gelatins, collagens, starches, hyaluronic acids, pectins, agar, polyacrylates, polyvinyl amines, polyvinyl acetates, polyethylene glycols, polyethylene oxides, polyvinyl pyrrolidones, polyurethanes or additional non-gelling polymers such as, for example, polyolefins, cellulose, cellulose derivatives, regenerated cellulose such as viscose, polyamides, polyacrylonitriles, polyvinyl chlorides, chitosans, polylactides, polyglycolides, polyester amides, polycaprolactones, polyhexamethylene terephthalates, polyhydroxybutyrates, polyhydroxyvalerates or polyesters and added to the water-soluble polyvinyl alcohol. The above-mentioned blends can be used as homopolymers or copolymers. It is also possible to use block copolymers and/or graft copolymers and/or block graft copolymers, statistical or alternating systems and any mixtures of these with each other.

The term alginates refers to the salts of alginic acid, a polymer that occurs naturally in algae, salts of the two uronic acids α-L-guluronic acid and β-D-mannuronic acid, which are 1,4-glycosidically linked. The term alginate includes E401, E402, E403, E404 and E405 (PGA). The term polyolefins includes PE, PB, PIB and PP. The term polyamides includes PA6, PA6.6, PA6/6.6, PA6.10, PA6.12 PA69, PA612, PA11, PA12, PA46, PA1212 and PA6/12. The term cellulose also includes regenerated cellulose such as viscose, as well as cellulose derivatives and chemically and/or physically modified cellulose. The term polyester includes PBT, BC, PET, PEN and UP.

The polyvinyl alcohol which is used for the production of the fibers made of polyvinyl alcohol or of which the polyvinyl alcohol fibers are made can be used with different degrees of hydrolysis and average molar masses.

The degree of hydrolysis of the polyvinyl alcohol is especially more than 70%, preferably more than 75%, even more preferably above 80% and up to 100%.

The mass average of the molar mass of the polyvinyl alcohol is especially preferably in the range from 20,000 to 200,000 g/mol, preferably in the range from 30,000 to 170,000 g/mol, especially preferably in the range from 40,000 to 150,000 g/mol, even more preferably in the range from 50,000 to 140,000 g/mol, even more preferably in the range from 70,000 to 120,000 g/mol.

The number average of the molar mass of polyvinyl alcohol is especially in the range from 10,000 to 120,000 g/mol, preferably in the range from 20,000 to 100,000 g/mol, especially preferably in the range from 20,000 to 80,000 g/mol, even more preferably in the range from 25,000 to 70,000 g/mol.

Fibers made of a first fiber raw material with a fiber titer of 0.5 dtex to 12 dtex can be used here. Preferably, they are used with a fiber titer of 1 dtex to 8 dtex, especially preferably with a fiber titer of 1.4 dtex to 7 dtex and even more preferably with a fiber titer of 1.4 dtex to 4 dtex. The term dtex or decitex refers to the weight of the fiber in grams at a theoretical length of 10,000 meters. Fibers with a filament titer below 0.5 dtex are less suitable.

The fibers made of a first fiber raw material can have a length between 30 mm and 100 mm. Preferably, they are used at a length of 30 mm to 90 mm, especially preferably at a length of 30 mm to 80 mm, and even more preferably at a length of 35 mm to 70 mm.

In particular, the fibers made of the first fiber raw material are so-called staple fibers that are used for the production of staple fiber nonwovens.

Moreover, the fibers or fibrous structures can also have additional fibers made of at least one second fiber raw material. In this context, the second fiber raw material can be configured to be gelling or non-gelling. Thus, gelling or non-gelling fibers can be used as the additional fibers.

Advantageously, a desired behavior of the fibers or fibrous structures can be systematically improved through the use of additional fibers. Thus, through the use of the additional fibers, the absorption capacity of the fibrous structure can be further increased and the shrinkage of the fibrous structure in an aqueous solution can be decreased.

Examples of the additional fiber raw material for the additional fibers include polyesters such as polyethylene terephthalate, water-insoluble polyvinyl alcohol, water-soluble polyvinyl alcohol that is water-soluble above a temperature of 50° C., polyolefins such as polyethylene or polypropylene, cellulose, cellulose derivatives, regenerated cellulose such as viscose, polyamides, polyacrylonitriles, chitosans, elastanes, polyvinyl chloride, polylactides, polyglycolides, polyester amides, polycaprolactones, plant-based natural fibers, alginates, modified chitosans, cellulose ethers such as carboxymethyl celluloses, methyl celluloses, ethyl celluloses, hydroxymethyl celluloses, hydroxyethyl celluloses, hydroxyalkylmethyl celluloses, hydroxypropyl celluloses, cellulose esters such as cellulose acetate, oxidized celluloses, bacterial celluloses, cellulose carbonates, gelatins, collagens, starches, hyaluronic acids, pectins, agar, polyvinyl amines, polyvinyl acetates, polyethylene glycols, polyethylene oxides, polyvinyl pyrrolidones, polyurethanes and/or polyacrylates. The listed second fiber raw materials can be used homopolymers and also as copolymers. It is also possible to use block copolymers and/or graft copolymers and/or block graft copolymers, statistical or alternating systems and any mixtures of these with each other.

It is also possible to simultaneously use additional gelling and non-gelling fibers or mixtures of various additional fibers. Preference is given here to the use of additional fibers made of polyamide, polyester, water-insoluble polyvinyl alcohol or polyvinyl alcohol that dissolves above a temperature of 50° C., polyacrylate, polyacrylic acid and even more preferably made of polyester or water-insoluble polyvinyl alcohol or polyvinyl alcohol that dissolves above a temperature of 50° C. and/or mixtures thereof.

The additional fibers can also be made of a second fiber raw material that is configured as a polymer blend. In this context, the advantages already cited for the first fiber raw material are also attained for the additional fibers.

The fibers made of the first fiber raw material or of the additional fiber raw material can also be used in the form of bi-component fibers and/or multi-component fibers. In this context, the bi-component fibers and/or multi-component fibers can be present in geometric shapes such as "core shell", "side-by-side", "pie or orange-type", "matrix with fibrils".

The bi-component fibers and/or multi-component fibers of the additional fiber raw material can be used for the thermal bonding of the nonwovens. When these fibers are heated, the nonwoven is thermally bonded. For example, with a core-shell fiber, the shell portion melts, thereby bonding the nonwoven. Examples of bi-component fibers and/or multi-component fibers that can be used are fibers of the additional fiber raw material made of polyethylene/polypropylene, polyethylene/polyester, co-polyester/polyethylene terephthalate, polyamide 6/polyamide 6.6, polybutylene terephthalate/polyethylene terephthalate.

Advantageously, through the use of additional fibers, the capacity to absorb water, especially a 0.9% solution of sodium chloride or of a Test Solution A cited in DIN 13726-1 under Point 3.2.2.3, can be markedly increased in comparison to fibrous structures without additional fibers, since, especially due to the non-gelling fibers, it is possible to reduce a gel-blocking effect that, above a predetermined saturation, prevents the additional absorption of water, especially of a 0.9% solution of sodium chloride or of a Test Solution A cited in DIN 13726-1 under Point 3.2.2.3. Moreover, the shrinkage of the fibrous structures containing fibers made of the first fiber raw material in an aqueous solution can be markedly decreased by admixing additional fibers.

In this context, the shrinkage of at least two-dimensional fibrous structures can be determined by stamping out pieces measuring 10.0 cm×10.0 cm (surface area 1) and immersing them into a 0.9% aqueous solution of sodium chloride or into a Test Solution A cited in DIN 13726-1 under Point 3.2.2.3. The stamped-out and impregnated pieces are removed from the solution and allowed to drip off for 2 minutes. Then the size of the pieces is measured (surface area 2). The shrinkage of the nonwovens can then be calculated according to the following formula:

$$\text{shrinkage}[\%] = 100 - \left(\frac{\text{surface area 2}[cm^2]}{\text{surface area 1}[cm^2]}\right) \times 100$$

The content of additional fibers in the fibrous structures can be between 1% and 70% by weight. Preferably, the content is 1% to 65% by weight, especially preferably 5% to 60% by weight, even more preferably 10% to 50% by weight, even more preferably between 15% and 40% by weight.

The additional fibers can have a fiber titer of 0.5 dtex to 12 dtex. Preferably, they are used with a fiber titer of 1 dtex to 8 dtex, especially preferably with a fiber titer of 1.4 dtex to 7 dtex, and even more preferably with a fiber titer of 1.4 dtex to 4 dtex. The term dtex or decitex refers to the weight of the fiber in grams at a theoretical length of 10,000 meters. Fibers with a filament titer below 0.5 dtex are less suitable.

The additional fibers can have a length between 30 mm and 100 mm. Preferably, they are used at a length of 30 mm to 90 mm, especially preferably at a length of 30 mm to 80 mm and even more preferably at a length of 35 mm to 70 mm.

In particular, the additional fibers made of the additional fiber raw material are so-called staple fibers that are used for the production of staple fiber nonwovens.

Moreover, the fibers or fibrous structures can also contain additives. Examples of possible additives are pharmacological active ingredients or drugs such as antibiotics, analgesics, anti-infectives, anti-inflammatories, wound-healing agents or the like, antimicrobial agents, antibacterial or antiviral agents, hemostatic agents, enzymes, amino acids, antioxidants, peptides and/or peptide sequences, polysaccharides (e.g. chitosan), growth factors (e.g. purines, pyrimidines), living cells, tricalcium phosphate, hydroxyapatite, particularly special hydroxyapatite nanoparticles, odor-absorbing additives such as activated charcoal, cyclodextrines, metals such as silver, gold, copper, zinc, carbon compounds such as activated charcoal, graphite or the like, cosmetic ingredients, vitamins and/or processing auxiliaries such as surface-active substances, cross-linking agents, brighteners, antistatic agents.

Moreover, through the use of at least one additive, the fibers or fibrous structures can advantageously be imparted with other physical, chemical and biological properties. Thus, for instance, an antibacterial effect of the fibers or fibrous structures can be attained by providing the fibers or fibrous structures with a finish consisting of silver or silver salts or antimicrobial agents such as polyhexanide (polyhexamethylene biguanide), chlorohexidine, cetylpyridinium chloride, benzalkonium chloride, Medihoney, PVP-iodine, hydrogen peroxide, 8-quinolinol, chloroamine, ethacridine lactate, nitrofural, or octenidine (N-octyl-1-[10-(4-octyliminopyridine-1-yl)decyl]pyridine-4-imine).

For example, the fibers or fibrous structures can be provided with an ethanolic solution containing an antimicrobial agent. Preferably, a padding machine provides the fibers or fibrous structures with a finish consisting of an ethanolic solution containing an antimicrobial agent such as polyhexanide, octenidine or silver salt. However, any other coating methods are also options. Moreover, the fibers or fibrous structures can be finished with an aqueous solution containing the antimicrobial agent. Preferably, during the application from an aqueous solution, a controlled quantity of water is used with which the fibers or fibrous structures undergo hydrogelling non-irreversibly and also change in terms of their morphological structure. In particular, coating methods such as foam application, kiss coaters and the like are possibilities.

The fibrous structures according to the invention can have a weight per unit area of 10 to 1000 $g/m^2$. In the case of two-dimensional fibrous structures, the weight per unit area is preferably from 10 to 700 $g/m^2$, especially preferably from 20 to 600 $g/m^2$, even more preferably from 50 to 500 $g/m^2$, even more preferably from 70 to 450 $g/m^2$, even more preferably from 80 to 350 $g/m^2$, even more preferably from 80 to 250 $g/m^2$, even more preferably from 90 to 220 $g/m^2$, even more preferably from 100 to 200 $g/m^2$.

In the case of two-dimensional fibrous structures, the thickness of the fibrous structure is preferably in the range from 0.2 mm to 10 mm, preferably in the range from 0.5 mm to 8 mm, even more preferably in the range from 0.7 mm to 7 mm, even more preferably in the range from 0.8 mm to 6 mm, even more preferably in the range from 0.9 mm to 5 mm, especially preferably in the range from 1.0 mm to 4 mm.

In the case of two-dimensional fibrous structures, they are preferably bonded thermally or mechanically. Especially preferably, they are bonded mechanically by means of needle-punching. Here, the needle-punching density is preferably in the range from 70 to 200 penetrations per square centimeter, especially preferably in the range from 70 to 170 penetrations per square centimeter, especially preferably in the range from 80 to 150 penetrations per square centimeter, especially preferably in the range from 100 to 150 penetrations per square centimeter.

The fibrous structures according to the invention can have a particularly high maximum breaking force in the lengthwise as well as in the crosswise direction of the fibrous structure in the hydrogelled state. For example, fibrous structures according to the invention that have a weight per unit area of 140 to 220 $g/m^2$ and that were bonded mechanically by needle-punching, for example, with a penetration density of 100 to 150 penetrations per square centimeter, have a maximum breaking force in the hydrogelled state of more than 0.3 N/2 cm. The preferred maximum breaking force in the hydrogelled state is more than 0.4 N/2 cm, even more preferably more than 0.5 N/2 cm, even more preferably more than 0.8 N/2 cm, even more preferably more than 1.0 N/2 cm, even more preferably more than 1.5 N/2 cm, even more preferably more than 2.0 N/2 cm and/or less than 50 N/2 cm, and/or less than 40 N/2 cm, and/or less than 35 N/2 cm. Accordingly, the maximum breaking force in the hydrogelled state is in the range from 0.3 N/2 cm to 50 N/2 cm, even more preferably from 0.4 N/2 cm to 40 N/2 cm, even more preferably from 0.5 N/2 cm to 30 N/2 cm, even more preferably from 0.8 N/2 cm to 25 N/2 cm, even more preferably from 1 N/2 cm to 25 N/2 cm, even more preferably from 1.5 N/2 cm to 25 N/2 cm, even more preferably from 2 N/2 cm to 25 N/2 cm.

The fibrous structures according to the invention can have an especially high maximum breaking elongation in the lengthwise as well as in the crosswise direction of the fibrous structure in the hydrogelled state. The preferred maximum breaking elongation in the hydrogelled state is 20% to 300%, especially preferably at 30% to 250%, even more preferably 50% to 200%, even more preferably 70% to 200%, even more preferably 80% to 200%, even more preferably 90% to 190%, even more preferably 90% to 180%. For example, fibrous structures according to the invention that have a weight per unit area of 140 $g/m^2$ to 220 $g/m^2$ and that were mechanically bonded by needle-punching, for example, with a penetration density of 100 to 150 penetrations per square centimeter, have the above-mentioned maximum breaking force values.

In another aspect of the invention, a method for the production of fibers or fibers or fibrous structures configured to be hydrogelling are proposed in which fibers or fibrous structures made of a first water-soluble fiber raw material comprising polyvinyl alcohol and/or unsubstituted or partially unsubstituted polyvinyl alcohol copolymer are tempered at a predetermined tempering temperature that is preferably higher than the glass transition temperature and/or lower than the melting temperature of the first fiber raw material employed, as well as for a predetermined duration, as a result of which the fibers are cross-linked.

Advantageously, fibers or fibrous structures having the hydrogelling properties can be produced by means of this very simple process. Here, only one single process step is needed in order to stabilize the fibers or fibrous structures, and moreover, it is configured so environmentally friendly that no solvents, by-products or waste products are generated. Furthermore, impurities that might be present in the fibers or fibrous structures such as, for instance, brighteners, spinning auxiliaries or solvents can be removed by means of the tempering.

The predetermined tempering temperature is preferably selected in such a way that it is higher than the glass transition temperature of the first fiber raw material employed. Moreover, the predetermined tempering temperature can be selected in such a way that it is lower than the melting temperature of the first fiber raw material employed. If several fibers made of different fiber raw materials are used, then the predetermined temperature is preferably selected in such a way that it preferably lies below the melting temperature or decomposition temperature of all of the fiber raw materials employed.

In many application cases, advantageous tempering temperatures have proven to be in a temperature range from 85° C. to 220° C., especially preferably from 100° C. to 200° C., even more preferably from 120° C. to 190° C., even more preferably between 130° C. and 180° C., especially preferably between 140° C. and 180° C., even more preferably between 150° C. and 175° C.

The predetermined tempering duration can be from 10 minutes to 14 hours. Preferably, the tempering duration ranges from 10 minutes to 10 hours, especially preferably from 10 minutes to 8 hours, even more preferably from 10 minutes to 7 hours, even more preferably from 10 minutes to 6 hours, even more preferably from 10 minutes to 5 hours, even more preferably between 20 minutes and 5 hours, even more preferably from 30 minutes to 5 hours, even more preferably from 30 minutes to 4 hours.

By selecting such tempering temperatures and tempering times, the cross-linking according to the invention of the fibers or fibrous structures can be carried out in a way that is especially gentle on the fibers or fibrous structures. Moreover, through the selection of these tempering conditions, the properties of the fibers or fibrous structures can be selected optimally. Thus, through the selection of these tempering conditions, the fibers or fibrous structures have a high absorption capacity and retention capacity as well as a very high maximum breaking force and maximum breaking elongation in the hydrogelled state. The tempering temperatures and the tempering times can be varied in order to achieve a differently configured cross-linking, so that the cross-linked fibers or fibrous structures have different properties, if desired. Moreover, through the selection of these tempering conditions, any impurities that might be present in the fibers or fibrous structures such as solvent residues or fiber auxiliaries and fiber processing agents such as brighteners, cross-linking agents, antistatic agents can even be reduced to a content that is below the detection limit. This is especially advantageous for the use of the fibers or fibrous structures in wound dressings since the above-mentioned impurities or fiber auxiliaries and fiber processing agents might be toxicologically unsafe.

Particularly before or after the tempering, a method can be used to obtain one-dimensional, two-dimensional or three-dimensional fibrous structures. Here, the appertaining fibrous structure can be produced from the fibers, for example, by means of one of the above-mentioned methods.

Advantageously, such a bonding method can be used to impart a desired shape to the fibers or fibrous structures and to bond them in this shape.

Moreover, additional fibers made of at least a second fiber raw material can be admixed.

Furthermore, an after-treatment can be carried out. Moreover, an admixture of processing auxiliaries is possible, especially before the bonding process. An admixture, for instance, of the above-mentioned additives can likewise be carried out.

A possible after-treatment can be an after-bonding, a sterilization such as, for example, radiation sterilization or sterilization with ethylene oxide, an irradiation, a coating, a finishing, an application of brighteners, a chemical modification or further processing such as, for example, a Raschel process, or the incorporation of reinforcement fibers.

An especially preferred after-treatment of the fibers or fibrous structures is a plasma treatment, especially in order to increase the hydrophilia of the fibers or fibrous structures. Plasma is a mixture of neutral and charged particles. In special cases, only changed particles are present. Various species such as electrons, cations, anions, neutral atoms, neutral or charged molecules are present in the plasma. The active particles present in the plasma can be used to modify surfaces such as, for example, fibers or nonwovens. Here, various effects can be achieved such as, for instance, a change in the surface by means of plasma etching, plasma activation or plasma polymerization. During plasma activation, the surface is activated by a plasma with the addition of oxygen. During plasma polymerization, additional organic precursor compounds are placed into the processing chamber.

By means of tempering, the fibers or fiber auxiliaries can be configured so as to be hydrophobic, since the tempering can reduce the need for fiber auxiliaries and fiber processing agents. The plasma treatment can be carried out under atmospheric pressure as well as in a vacuum, especially with the addition of oxygen. Additional substances such as acrylic acid can also be added during the plasma treatment.

Moreover, a preferred after-treatment is the sterilization of the fibers or fibrous structures for use especially in wound dressings. Preferably, the sterilization is carried out by radiation sterilization or by sterilization with ethylene oxide. The sterilization can positively influence the properties such as, for example, the absorption capacity and/or the maximum breaking force and maximum breaking elongation in the hydrogelled state.

The individual process steps of tempering, bonding, admixing additional fibers, incorporating additives, adding processing auxiliaries and carrying out an after-treatment can be repeated several times in any desired sequence. In this context, it has proven to be advantageous to temper the fibers or fibrous structures at least once at a predetermined tempering temperature for a predetermined tempering duration.

Examples of processing auxiliaries include brighteners, antistatic agents, surfactants, stabilizers, gliding agents and the like.

In a preferred variant of the production method, the fibers made of a first fiber raw material, especially water-soluble polyvinyl alcohol staple fibers, are tempered for purposes of cross-linking at a predetermined tempering temperature that is higher than the glass transition temperature and lower than the melting temperature of the fibers made of a first fiber raw material, especially for 10 minutes to 7 hours. Subsequently, an option is to admix additional fibers, especially non-gelling fibers, especially preferably polyester fibers, having a content of 10% to 50% by weight. The fibers thus produced can then be used to make a two-dimensional fibrous structure such as, for instance, a nonwoven, if so desired, with the use of processing auxiliaries such as brighteners or antistatic agents, by means of a bonding process.

In another preferred variant of the production process, fibers made of a first fiber raw material can optionally be mixed with fibers from a second fiber raw material, whereby the content of additional fibers is preferably between 10% and 50% by weight. However, it is also possible to use only fibers made of a first fiber raw material. Preferably, polyvinyl alcohol fibers are used as the fibers made of a first fiber raw material, and polyester fibers are used as the additional fibers made of a second fiber raw material. A two-dimensional fibrous structure such as, for example, a nonwoven, can be made of these fibers by means of a bonding process. Subsequently, the two-dimensional fibrous structure thus produced can be tempered at a tempering temperature above the glass transition temperature and below the melting temperature of the fibers made of a first fiber raw material. Optionally, a two-dimensional fibrous structure thus produced can be after-treated.

In another aspect of the invention, the use of fibers or fibrous structures as described above is proposed, whereby such fibers or fibrous structures are used especially for the production of materials for medical applications, especially for wound dressings and wound bandages, and particularly for the production of wound dressings for the realm of modern wound care.

Moreover, the fibers or fibrous structures can be used for the production of other materials for medical applications such as stitching materials, implants, tissue engineering scaffolds, transdermal patches, drug-delivery products, support materials or ostomy products.

It is also possible to use the fibers or fibrous structures for the production of support material, insulating materials and filter materials for the manufacture of hygiene, cosmetic and household products as well as technical absorber products such as cable sheathing, products for the food sector as well as for food packaging. Hygiene products can include sanitary napkins, diapers and incontinence products. The household products likewise include cleaning materials.

For each individual application, the above-mentioned advantages, among others, come to the fore.

Another aspect of the invention that is proposed is a wound bandage or a wound dressing containing fibers or fibrous structures as described above. Such fibers or fibrous structures can preferably be used in the realm of modern wound care, especially for modern (moist) wound treatment.

In modern wound care, the wound dressings provide an optimal moist wound environment in which the wound can heal more quickly. Modern wound care is used for the treatment of wounds that are difficult to heal such as chronic wounds caused, for instance, by pressure stress or bedsores (decubitus), diabetes, circulatory disorders, metabolic disorders, vascular diseases such as venous insufficiency or immunological diseases.

The fibers or fibrous structures according to the invention have a high absorption capacity for aqueous solutions and can thus absorb and enclose the wound exudate. Moreover, by picking up the wound exudate, the fibers or fibrous structures form a hydrogel that firmly encloses the fluid and holds it back, even under pressure that arises, for example, when a bandage is placed onto it. The formation of the hydrogel also creates a moist wound environment by means of which healing of the wound is promoted. The hydrogelled fibers or fibrous structures adapt to the structure of the wound surface and can especially be used for the treatment of wound cavities. Thanks to the high maximum breaking force and maximum breaking elongation, the hydrogelled fibers or fibrous structures can easily be removed in one piece from the wound or from the wound cavity, without damaging it.

Such wound bandages or wound dressings can also be used in a manner that is analogous to classic wound bandages or wound dressings such as, for example, gauze bandaging material, but they have the advantageous hydrogelling properties, so that the wound bandages or wound dressings according to the invention translate into wound care that is advantageously improved.

Execution of the Invention
Methodology and Measurement Methods

The manner in which various parameters that can be employed to characterize the fibers or fibrous structures according to the invention should be determined will be presented below:

1) Determination of the thickness of the two-dimensional fibrous structures and/or nonwoven In accordance with DIN EN ISO 9073-2, but without conditioning 2) Determination of the weight per unit area of the two-dimensional fibrous structures and/or nonwoven In accordance with DIN EN 29073, but without conditioning 3) Determination of the absorption capacity of fibers A 600-ml flask is filled with 300 ml of a 0.9% solution of sodium chloride (0.9 g sodium chloride dissolved in 100 ml of distilled water) or with a solution according to the Test Solution A cited in DIN 13726-1 under Point 3.2.2.3. Then, 0.40 g (fiber weight, dried: $m_{dry}$) of the fibers are stirred into the solution. The fibers remain in the flask for 10 min while being stirred occasionally by means of a glass rod. The time is kept using a stopwatch. A pre-tared metal screen (32-mesh) is placed onto a 2000-ml flask. The entire content on the 600-ml flask is poured through the metal screen. The fibers are allowed to drip off for 5 minutes in the metal screen. The weight of the metal screen including the fibers is determined. The tare of the metal screen is subtracted from the weight. The result is the fiber weight of the hydrogelled fibers ($m_{wet}$).

The absorption capacity of the fibers is determined employing the following formula: relative absorption capacity $$[g/g] = \frac{m_{wet} - m_{dry}}{m_{dry}}$$

wherein
$m_{wet}$ stands for the mass of the test specimen and the absorbed liquid at the end of the test, in grams
$m_{dry}$ stands for the mass of the dry test specimen, in grams 4) Determination of the absorption capacity of two-dimensional fibrous structures or nonwovens based on DIN EN ISO 9073-6

The absorption capacity is tested on the basis of DIN EN ISO 9073-6; Absorption of liquids.

A 0.9% solution of sodium chloride (0.9 g of sodium chloride in 100 ml of distilled water) or the Test Solution A according to DIN 13726-1 under Point 3.2.2.3 is used as the prepared liquid (test medium) according to Point 5.2.7 in DIN EN ISO 9073-6.

The test medium employed is also indicated for each test result.

The test specimens (measuring 10 cm×10 cm) are prepared and the determination is carried out analogously to DIN EN ISO 9073-6, but without conditioning.

Diverging from the standard, the absorption capacity was also determined after two different absorption times:

1) Absorption capacity after 1 minute: according to the standard, the test specimens are immersed into the test medium for 1 minute and then allowed to drip off for 2 minutes
2) Absorption capacity after 1 hour: the test specimens are immersed into the test medium for 1 hour and then allowed to drip off for 2 minutes The absorption of liquid (LAC) in percent is calculated according to DIN EN ISO 9073-6 on the basis of the following formula:

$$LAC[\%] = \frac{m_n - m_k}{m_k} \times 100$$

wherein
$m_k$ stands for the mass of the dry test specimen, in grams
$m_n$ stands for the mass of the test specimen and the absorbed liquid at the end of the test, in grams The relative absorption, in g/g is calculated as follows:

$$\text{relative absorption } [g/g] = \frac{m_n - m_k}{m_k}$$

The absolute absorption, in g/m² is calculated as follows:

absolute absorption [g/m²]=relative absorption [g/g]×weight per unit area [g/m²]

After the determination of the absorption capacity, the hydrogelled test specimens are still used after 1 hour to determine the retention capacity of two-dimensional fibrous structures and/or nonwovens (Point 5) and to determine the soluble content of two-dimensional fibrous structures and/or nonwovens (Point 6).

5) Determination of the retention capacity of two-dimensional fibrous structures or nonwovens After the determination of the absorption capacity (Point 4), the hydrogelled test specimens are used after 1 hour (absorption capacity after 1 hour) for determination purposes; moreover, the values ascertained for the masses of the dry test specimens that had been ascertained during the determination of the absorption capacity were employed:

$m_k$ stands for the mass of the dry test specimen, in grams

The test specimens are each laid onto a flat metal net measuring 15 cm×15 cm, which is placed over a bowl so that liquid from the test specimen can drain into the bowl. A weight is placed flat onto the test specimen and it exerts a pressure of 40 mmHg over the entire surface area of the test specimen (this corresponds to a weight of 5.434 kg on a surface area of 100 cm²) over a time period of 2 minutes. Afterwards, the weight of the test specimen is precisely weighed ($m_{pressure}$).

The relative retention capacity in g/g is calculated as follows:

$$\text{relative retention capacity } [g/g] = \frac{m_{pressure} - m_k}{m_k}$$

The retention capacity in percent is calculated as follows:

$$\text{retention capacity } [\%] = \frac{\text{relative retention capacity}}{\text{relative absorption after 1 hour}} \times 100$$

6) Determination of the soluble content of two-dimensional fibrous structures or nonwovens After the determination of the absorption capacity (Point 4), the hydrogelled test specimens are used after 1 hour (absorption capacity after 1 hour) for determination purposes; moreover, the values ascertained for the masses of the dry test specimens that had been ascertained during the determination of the absorption capacity were employed:

$m_k$ stands for the mass of the dry test specimen, in grams

The hydrogelled test specimen is placed into a tared 100-ml flask ($m_{flask}$). The flask with the test specimen is placed into a commercially available laboratory drying cabinet with circulating air at a temperature of 70° C., so that the hydrogelled test specimen dries. After 24 hours, the flask with the dried test specimen is removed from the drying cabinet. After cooling, the weight of the test specimen ($m_{dry}$) is determined, whereby the flask is weighed together with the test specimen ($m_{total}$) and the weight of the flask is subtracted from the weight:

$m_{dry} = m_{total} - m_{flask}$

The soluble content in percent is calculated as follows:

$$\text{soluble content}[\%] = 100 - \left(\frac{m_{dry}}{m_k} \times 100\right)$$

7) Determination of the shrinkage of two-dimensional fibrous structures or nonwovens The shrinkage is determined by stamping out pieces measuring 10.0 cm×10.0 cm (surface area 1) and immersing them into a test medium. The test medium is either a 0.9% aqueous solution of sodium chloride or the Test Solution A according to DIN 13726-1 under Point 3.2.2.3. Each test medium is also indicated for each test result.

The stamped-out and impregnated pieces are removed from the solution after 1 hour and allowed to drip off for 2 minutes. Then, the size of the pieces is measured (surface area 2). The shrinkage of the nonwovens can then be calculated according to the following formula:

$$\text{shrinkage}[\%] = 100 - \left(\frac{\text{surface area 2}[cm^2]}{\text{surface area 1}[cm^2]}\right) \times 100$$

8) Determination of the maximum breaking force and of the maximum breaking elongation at maximum tensile force of two-dimensional fibrous structures and/or nonwovens in the hydrogelled state For the determination, pieces of nonwoven the size of a DIN-A4 sheet of paper were stamped out and placed into an excess quantity of a 0.9% solution of sodium chloride or of Test Solution A according to DIN 13726-1 under Point 3.2.2.3. The nonwoven pieces are removed from the solution after 1 hour. A stamping iron is employed to stamp the test specimens out of the hydrogelled nonwoven pieces in the lengthwise direction (machine direction) of the nonwoven as well as in the crosswise direction of the nonwoven.

The stamping iron used for stamping out the test specimen has a length of 90 mm. The width at the top and bottom ends amounts to 35 mm. After 20 mm, both ends of the stamping iron taper down to 20 mm (see FIG. 1).

The maximum breaking force and maximum breaking elongation are then determined according to EN 29073-03 on a Zwick Z 1.0, but with the following differences:
  no conditioning
  draw-off speed of 200 mm/min
  a different stamping iron (as described above); clamping length adapted to the length of the stamping iron
  different preparation of the specimen: the specimens are not measured in the dry state, but rather on the hydrogelled state (the test specimens are made as described above)

9) Determination of the solubility of water-soluble fibers

A 250-ml flask is filled with 200 ml of distilled water and heated to the test temperature (temperature at which the fibers made of polyvinyl alcohol are water-soluble) using a hotplate. The temperature is controlled using a thermometer.

In each case, 0.4 g of the fibers are briefly stirred into 200 ml of the tempered water. The fibers are first left in the flask for 3 minutes without being stirred. Subsequently, the content of the flask is vigorously stirred for 7 minutes. The time is kept using a stopwatch. Finally, there is a visual inspection (with the naked eye) to see whether the fibers have dissolved completely. The water solubility is considered to be 100 percent once no solid fibers or fiber components can be seen in the solution.

10) Determination of the thermodesorption

For the determination of the thermodesorption, a specimen consisting of fibers or fibrous structures is heated up at 150° C. for 20 minutes in order to release the organic components contained in the fibers; a cryotrap is employed for focusing and then the components are injected into a gas chromatography-mass spectrometry (GC/MS) device by means of a programmed temperature vaporizing (PTV) injector. A GERSTEL thermodesorption system and a GERSTEL PTV injector are used for this purpose. The released components are detected by means of GC/MS. A GC Agilent Technologies 6890N Network GC System, Mass Selective Detector Agilent Technologies 5973, is utilized in the process.

11) Determination of the wetting time of two-dimensional fibrous structures or nonwovens The time needed for one drop of distilled water to soak into the fibrous structures or into the nonwoven is measured. The test is carried out with a total of five drops and the mean value is then ascertained.

12) Examination of the fibers or fibrous structures by means of XPS

The measurements by means of XPS (X-ray photoelectron spectroscopy) were carried out on a SSX-100 spectrometer (SSI company, United States) with monoenergetic Al K$\alpha$1,2 excitation (1486.6 eV) in an ultra-high vacuum (10-9 Torr). The information depth is between 6 nm and 10 nm. The charge compensation for non-conductive specimens is obtained by means of a flood gun. Prior to the start of the measurement, the specimens were stored in a vacuum overnight.

EXAMPLES

Example 1

Production of the Tempered Fibers Made of Water-soluble Polyvinyl Alcohol

Water-soluble staple fibers made of polyvinyl alcohol (2.2 dtex, 51 mm) are opened up with a fiber bale opener. The staple fibers made of polyvinyl alcohol are water-soluble at a temperature below 25° C. After the fiber bale has been opened, the fibers are tempered at 150° C. (for example, in a commercially available laboratory drying cabinet with air circulation) in order to bring about cross-linking of the polyvinyl alcohol. The stability of the PVA fibers sets in after a tempering duration of 2 hours, and this is manifested in the formation of stable, hydrogelling fibers in a 0.9% aqueous solution of sodium chloride or in the Test Solution A according to DIN 13726-1 under Point 3.2.2.3. The stability of the fibers rises as the tempering duration increases. At a tempering duration of 4 to 7 hours, the fibers exhibit a high stability.

After the tempering, the absorption of a 0.9% aqueous solution of sodium chloride by the fibers is determined. The determination of the absorption is carried out as described in Measuring Methods under Point 3 (Determination of the absorption capacity of fibers). The relative absorption capacity for a 0.9% aqueous solution of sodium chloride as the test medium amounts to 3 to 40 g/g, depending on the tempering duration and thus on the degree of cross-linking The tempered fibers made of polyvinyl alcohol can be further processed into nonwovens. Nonwovens are made of polyvinyl alcohol fibers or of polyvinyl alcohol fibers with the admixture of other fibers such as, for instance, polyester. The nonwovens made of the tempered PVA fibers, depending on the fiber admixture and on the degree of cross-linking, have a high relative absorption capacity of 4 to 35 g/g for a 0.9% aqueous solution of sodium chloride as the test medium.

Example 2

Needle-bonded Nonwovens Made of Water-soluble Polyvinyl Alcohol Fibers with Subsequent Thermal Cross-linking A needle-bonded nonwoven is made of water-soluble polyvinyl alcohol staple fibers. The polyvinyl alcohol fibers are water-soluble at a temperature below 25° C. and exhibit a fiber titer of 1.7 dtex or 2.2 dtex at a staple fiber length of 38 mm or 51 mm. The polyvinyl alcohol fibers are laid by means of a stripper to form a nonwoven and subsequently needle-punched at a penetration density of 100 to 170 penetrations per square centimeter. The needle-bonded polyvinyl alcohol nonwovens are tempered at 150° C. in order to achieve a stabilization of the polyvinyl alcohol. The nonwovens are tempered here in a commercially available laboratory drying cabinet with air circulation. The stability of the polyvinyl alcohol nonwovens sets in after a tempering duration of 2 hours, and this is manifested in the formation of stable, hydrogelling fibers in a 0.9% aqueous solution of sodium chloride or in the Test Solution A according to DIN 13726-1 under Point 3.2.2.3. The stability of the nonwovens rises as the tempering duration increases. At a tempering duration of 2.5 to 7 hours, the nonwovens exhibit a high stability. The soluble content of the nonwovens is at a maximum of 20% after 1 hour in the Test Solution A. After the tempering, the relative absorption capacity is determined with the Test Solution A as the test medium after 1 minute and after 1 hour. The relative absorption capacity after 1 minute is between 5 and 20 g/g. The relative absorption capacity after 1 hour is between 5 and 20 g/g. Moreover, the retention capacity of the nonwovens after 1 hour in the Test Solution A was determined. This value is between 80% and 100%. Furthermore, the shrinkage of the bonded nonwovens after 1 hour in the Test Solution A was determined. The shrinkage of polyvinyl alcohol nonwovens amounts to between 30% and 60%, depending on the tempering duration and thus on the degree of cross-linking of the nonwovens.

TABLE 1

Example of a tempered needle-bonded nonwoven made of water-soluble polyvinyl alcohol fibers

| Parameter | Description/Result |
| --- | --- |
| polyvinyl alcohol fibers | 1.5 dtex to 2.2 dtex, 40 mm to 70 mm |
| temperature at which the polyvinyl alcohol fibers are water-soluble | below 25° C. |
| content of polyvinyl alcohol fibers [%] | 100 |
| tempering duration at 150° C. [min] | 150 to 300 |
| type of bonding | needle-punching |
| penetration density [#/cm$^2$] | 100 to 170 |
| weight per unit area [g/m$^2$] | 150 to 210 |
| thickness [mm] | 1.5 to 3.0 |
| relative absorption capacity [g/g] after 1 minute in the Test Solution A | 5.0 to 20.0 |
| relative absorption capacity [g/g] after 1 hour in the Test Solution A | 5.0 to 20.0 |
| retention capacity [%] after 1 hour in the Test Solution A | 80 to 100 |
| soluble content after 1 hour in the Test Solution A [%] | 0 to 20 |
| shrinkage [%] | 30 to 50 |
| maximum breaking force in the hydrogelled state [N/2 cm]; lengthwise | 1 to 20 |

TABLE 1-continued

Example of a tempered needle-bonded nonwoven made of water-soluble polyvinyl alcohol fibers

| Parameter | Description/Result |
|---|---|
| maximum breaking elongation in the hydrogelled state [%]; lengthwise | 80 to 300 |
| maximum breaking force in the hydrogelled state [N/2 cm]; crosswise | 1 to 20 |
| maximum breaking elongation in the hydrogelled state [%]; crosswise | 80 to 300 |

Example 3

Calander-bonded Nonwovens Made of Water-soluble Polyvinyl Alcohol Fibers, with Subsequent Thermal Cross-linking A calander-bonded nonwoven is made of water-soluble polyvinyl alcohol staple fibers. The polyvinyl alcohol fibers are water-soluble at a temperature below 25° C. and have a fiber titer of 2.2 dtex at a staple fiber length of 51 mm. The polyvinyl alcohol fibers are laid by means of a stripper to form a nonwoven and subsequently bonded by thermal bonding using a calander with point seal (PS) gravure. The thermally bonded polyvinyl alcohol nonwovens are tempered at 150° C. in order to achieve a stabilization of the polyvinyl alcohol. The nonwovens are tempered here in a commercially available laboratory drying cabinet with air circulation. The stability of the polyvinyl alcohol nonwovens sets in after a tempering duration of 2 hours, and this is manifested in the formation of stable, hydrogelling fibers in a 0.9% aqueous solution of sodium chloride or in the Test Solution A according to DIN 13726-1 under Point 3.2.2.3. The stability of the nonwovens rises as the tempering duration increases. At a tempering duration of 2.5 to 7 hours, the nonwovens exhibit a high stability. The soluble content of the nonwovens is at a maximum of 20% after 1 hour in the Test Solution A. After the tempering, the relative absorption capacity is determined with the Test Solution A as the test medium after 1 minute and after 1 hour. The relative absorption capacity after 1 minute is between 5 and 20 g/g. The relative absorption capacity after 1 hour is between 5 and 20 g/g. Moreover, the retention capacity of the nonwovens after 1 hour in the Test Solution A was determined. This value is between 80% and 100%. Furthermore, the shrinkage of the bonded nonwovens after 1 hour in the Test Solution A was determined. The shrinkage of the polyvinyl alcohol nonwovens amounts to between 30% and 60%, depending on the tempering duration and thus on the degree of cross-linking of the nonwovens.

TABLE 2

Example of a tempered thermally bonded nonwoven made of water-soluble polyvinyl alcohol fibers

| Parameter | Description/Result |
|---|---|
| polyvinyl alcohol fibers | 2.2 dtex, 51 mm |
| temperature at which the polyvinyl alcohol fibers are water-soluble | below 25° C. |
| content of polyvinyl alcohol fibers [%] | 100 |
| tempering duration at 150° C. [min] | 150 to 300 |
| type of bonding | thermally with a calendar (PS gravure) |
| weight per unit area [g/m$^2$] | 150 to 210 |
| thickness [mm] | 0.8 to 3.0 |
| relative absorption capacity [g/g] after 1 minute in the Test Solution A | 5.0 to 20.0 |
| relative absorption capacity [g/g] after 1 hour in the Test Solution A | 5.0 to 20.0 |
| retention capacity [%] after 1 hour in the Test Solution A | 80 to 100 |
| soluble content after 1 hour in the Test Solution A [%] | 0 to 20 |
| shrinkage [%] | 20 to 50 |
| maximum breaking force in the hydrogelled state [N/2 cm]; lengthwise | 2 to 30 |
| maximum breaking elongation in the hydrogelled state [%]; lengthwise | 100 to 400 |
| maximum breaking force in the hydrogelled state [N/2 cm]; crosswise | 2 to 30 |
| maximum breaking elongation in the hydrogelled state [%]; crosswise | 100 to 400 |

Example 4

Blended Nonwovens Made of Water-soluble Polyvinyl Alcohol Fibers and Polyester Fibers, with Subsequent Thermal Cross-linking Needle-bonded blended nonwovens are made of water-soluble polyvinyl alcohol staple fibers (2.2 dtex) and polyester staple fibers. The content of polyester fibers in the blended nonwoven amounts to between 10% and 50%. The polyvinyl alcohol fibers are water-soluble at a temperature below 25° C. and have a fiber titer of 2.2 dtex at a staple fiber length of 51 mm. The polyester fibers have a fiber titer of 1.7 dtex or 3.3 dtex and a staple fiber length of 38 mm or 51 mm. The nonwovens are tempered at 150° C. in order to bring about cross-linking of the polyvinyl alcohol fibers in the nonwoven. The nonwovens are tempered here in a commercially available laboratory drying cabinet with air circulation. The stability of the polyvinyl alcohol nonwovens sets in after a tempering duration of 2 hours, and this is manifested in the formation of stable, hydrogelling nonwovens in a 0.9% aqueous solution of sodium chloride or in the Test Solution A according to DIN 13726-1 under Point 3.2.2.3. The stability of the nonwovens rises as the tempering duration increases. At a tempering duration of 2.5 to 7 hours, the nonwovens exhibit a high stability. The soluble content of the nonwovens is at a maximum of 20% after 1 hour in the Test Solution A. After the tempering, the relative absorption capacity is determined with the Test Solution A as the test medium after 1 minute and after 1 hour. The relative absorption capacity after 1 minute is between 7 and 25 g/g. The relative absorption capacity after 1 hour is between 7 and 25 g/g. Moreover, the retention capacity of the nonwovens after 1 hour in the Test Solution A was determined. This value is between 80% and 100%. Furthermore, the shrinkage of the bonded nonwovens after 1 hour in the Test Solution A was determined. The shrinkage of polyvinyl alcohol nonwovens amounts to between 1% and 45%, depending on the tempering duration and thus on the degree of cross-linking of the nonwovens. The shrinkage of the blended nonwovens is thus considerably lower in comparison to that of polyvinyl alcohol nonwovens without the admixture of polyester fibers. The shrinkage drops as the polyester content in the nonwoven increases.

TABLE 3

Example of a tempered needle-bonded nonwoven made of water-soluble polyvinyl alcohol fibers, with the admixture of polyester fibers

| Parameter | Description/Result |
| --- | --- |
| polyvinyl alcohol fibers | 2.2 dtex, 51 mm |
| temperature at which the polyvinyl alcohol fibers are water-soluble | below 25° C. |
| content of polyvinyl alcohol fibers [%] | 50 to 100 |
| polyester fibers | 1.7 dtex and 3.3 dtex, 38 mm and 51 mm |
| content of polyester fibers [%] | 0 to 50 |
| tempering duration at 150° C. [min] | 150 to 300 |
| type of bonding | mechanically by means of needle-punching |
| penetration density [#/cm$^2$] | 100-170 |
| weight per unit area [g/m$^2$] | 150 to 210 |
| thickness [mm] | 0.8 to 3.0 |
| relative absorption capacity [g/g] after 1 minute in the Test Solution A | 7.0 to 25.0 |
| relative absorption capacity [g/g] after 1 hour in the Test Solution A | 7.0 to 25.0 |
| retention capacity [%] after 1 hour in the Test Solution A | 80 to 100 |
| soluble content after 1 hour in the Test Solution A [%] | 0 to 30 |
| shrinkage [%] | 1% to 45% |
| maximum breaking force in the hydrogelled state [N/2 cm]; lengthwise | 4 to 30 |
| maximum breaking elongation in the hydrogelled state [%]; lengthwise | 100 to 400 |
| maximum breaking force in the hydrogelled state [N/2 cm]; crosswise | 4 to 30 |
| maximum breaking elongation in the hydrogelled state [%]; crosswise | 100 to 400 |

Example 5

Blended Nonwovens Made of Water-soluble Polyvinyl Alcohol Fibers and Polyvinyl Alcohol Fibers that are Water-soluble above a Temperature of 70° C., with Subsequent Thermal Cross-linking Needle-bonded blended nonwovens are made of water-soluble polyvinyl alcohol staple fibers (2.2 dtex) (water-soluble below 25° C.) and polyvinyl alcohol staple fibers that are water-soluble above a temperature of 70° C. The content of polyvinyl alcohol fibers that are water-soluble above a temperature of 70° C. is 20% and 35%. The water-soluble polyvinyl alcohol fibers are water-soluble at a temperature below 25° C. and have a fiber titer of 2.2 dtex at a staple fiber length of 51 mm. The polyvinyl alcohol fibers that are water-soluble at a temperature of 70° C. have a fiber titer of 1.7 dtex and a staple fiber length of 38 mm. The nonwovens are tempered at 150° C. in order to cross-link the water-soluble polyvinyl alcohol fibers in the nonwoven. The nonwovens are tempered here in a commercially available laboratory drying cabinet with air circulation. The stability of the polyvinyl alcohol nonwovens sets in after a tempering duration of 2 hours, and this is manifested in the formation of stable, hydrogelling nonwoven in a 0.9% aqueous solution of sodium chloride or in the Test Solution A according to DIN 13726-1 under Point 3.2.2.3. The stability of the nonwovens rises as the tempering duration increases. At a tempering duration of 2.5 to 7 hours, the fibers exhibit a high stability. The soluble content of the nonwovens is at a maximum of 20% after 1 hour in the Test Solution A. After the tempering, the relative absorption capacity is determined with the Test Solution A as the test medium after 1 minute and after 1 hour. The relative absorption capacity after 1 minute is between 7 and 25 g/g. The relative absorption capacity after 1 hour is between 7 and 25 g/g. Moreover, the retention capacity of the nonwovens after 1 hour in the Test Solution A was determined. This value is between 80% and 100%. Furthermore, the shrinkage of the bonded nonwovens after 1 hour in the Test Solution A was determined. The shrinkage of polyvinyl alcohol nonwovens amounts to between 1% and 45%, depending on the tempering duration and thus on the degree of cross-linking of the nonwovens. The shrinkage of the blended nonwovens is thus considerably lower in comparison to that of polyvinyl alcohol nonwovens without the admixture of the polyester fibers that are water-soluble above a temperature of 70° C. The shrinkage drops as the content of these fibers in the nonwoven increases.

TABLE 4

Example of a tempered needle-bonded nonwoven made of water-soluble polyvinyl alcohol fibers with an admixture of polyvinyl alcohol fibers that are water-soluble above a temperature of 70° C.

| Parameter | Description/Result |
| --- | --- |
| polyvinyl alcohol fibers | 2.2 dtex, 51 mm |
| temperature at which the polyvinyl alcohol fibers are water-soluble | below 25° C. |
| content of polyvinyl alcohol fibers [%] | 50 to 100 |
| polyvinyl alcohol fibers that are water-soluble above a temperature of 70° C. [%] | 1.7 dtex, 38 mm |
| content of polyvinyl alcohol fibers that are water-soluble above a temperature of 70° C. [%] | 0 to 50 |
| tempering duration at 150° C. [min] | 150 to 300 |
| type of bonding | mechanically by means of needle-punching |
| penetration density [#/cm$^2$] | 100 to 170 |
| weight per unit area [g/m$^2$] | 150 to 210 |
| thickness [mm] | 0.8 to 3.0 |
| relative absorption capacity [g/g] after 1 minute in the Test Solution A | 7.0 to 25.0 |
| relative absorption capacity [g/g] after 1 minute in the Test Solution A | 7.0 to 25.0 |
| retention capacity [%] after 1 hour in the Test Solution A | 80 to 100 |
| soluble content after 1 hour in the Test Solution A [%] | 0 to 30 |
| shrinkage [%] | 1% to 45% |
| maximum breaking force in the hydrogelled state [N/2 cm]; lengthwise | 4 to 30 |
| maximum breaking elongation in the hydrogelled state [%]; lengthwise | 100 to 400 |
| maximum breaking force in the hydrogelled state [N/2 cm]; crosswise | 4 to 30 |
| maximum breaking elongation in the hydrogelled state [%]; crosswise | 100 to 400 |

Example 6

Plasma Treatment of the Tempered Nonwovens, for Hydrophilization Purposes

A needle-bonded nonwoven is made of water-soluble polyvinyl alcohol staple fibers. The polyvinyl alcohol fibers are water-soluble at a temperature below 25° C. and have a fiber titer of 2.2 dtex at a staple fiber length of 51 mm. The polyvinyl alcohol fibers are laid by means of a stripper to form a nonwoven and subsequently needle-punched at a penetration density of 100 to 170 penetrations per square centimeter. The needle-bonded polyvinyl alcohol nonwovens are tempered at 150° C. in order to achieve a stabilization of the polyvinyl alcohol. The nonwovens are tempered here in a commercially available laboratory drying cabinet with air circulation over a period of time of 2.5 to 5 hours. After the tempering, the nonwovens are treated in a vacuum with plasma while oxygen is fed in, in order to increase the hydrophilia of the nonwovens. Alternatively, after the tempering, the nonwovens were treated with a plasma while oxygen and acrylic acid were fed in. In both plasma treatments, the wetting time was reduced from 2 minutes to 1 second to 10 seconds, thus significantly increasing the hydrophilia of the nonwovens.

Example 7

Application of Wetting Agents on the Tempered Nonwoven in Order to Increase the Hydrophilia A needle-bonded nonwoven is made of water-soluble polyvinyl alcohol staple fibers. The polyvinyl alcohol fibers are water-soluble at a temperature below 25° C. and have a fiber titer of 2.2 dtex at a fiber-staple length of 51 mm. The polyvinyl alcohol fibers are laid by means of a stripper to form a nonwoven and subsequently needle-punched at a penetration density of 100 to 170 penetrations per square centimeter. The needle-bonded polyvinyl alcohol nonwovens are tempered at 150° C. in order to achieve a stabilization of the polyvinyl alcohol. The nonwovens are tempered here in a commercially available laboratory drying cabinet with air circulation over a period of time of 2.5 to 5 hours. After the tempering, the nonwovens are sprayed with an aqueous solution containing a wetting agent or a film-forming agent that increases the hydrophilia of the nonwoven. For this purpose, aqueous solutions having a concentration of 5% to 20% are made from the wetting agent, surfactant or film-forming agent, and these solutions are then sprayed onto the nonwoven with a compressed-air spray gun. The following substances were employed as wetting agents, surfactants or film-forming agents: Tween 20, Conolan PG, Lertisan HD30, Lubricit 1136, Lubricit 1970, polyethylene glycol having a molecular weight of 400 g/mol.

The spraying of the nonwovens reduced the wetting time from 2 minutes to 1 second to 10 seconds, thus significantly increasing the hydrophilia of the nonwovens.

Example 8

Providing the Nonwovens with an Antimicrobial Finish from an Ethanolic Solution

A needle-bonded nonwoven is made of water-soluble polyvinyl alcohol staple fibers. The polyvinyl alcohol fibers are water-soluble at a temperature below 25° C. and have a fiber titer of 2.2 dtex at a fiber-staple length of 51 mm. The polyvinyl alcohol fibers are laid by means of a stripper to form a nonwoven and subsequently needle-punched at a penetration density of 100 to 170 penetrations per square centimeter. The needle-bonded polyvinyl alcohol nonwovens are tempered at 150° C. in order to achieve a stabilization of the polyvinyl alcohol. The nonwovens are tempered here in a commercially available laboratory drying cabinet with air circulation over a period of time of 2.5 to 5 hours. After the tempering, the nonwovens are provided with a polyhexanide finish by impregnating them with an ethanolic polyhexanide solution. A 0.4% solution of polyhexanide in ethanol (absolute) is prepared for this purpose. For example, a coating system having a padding machine and made by the Coatema company (Basecoater or Smartcoater) is employed for this purpose. The polyhexanide solution is placed into a padding-machine tank. The tempered nonwoven passes through the padding machine and is impregnated with the polyhexanide solution. Then, the solution is pressed into the nonwoven by means of pressure exerted by a roller. Subsequently, the nonwoven passes through a dryer at a temperature of 70° C. in order to dry the nonwoven. After having been finished with the polyhexanide solution, the nonwoven contains 1 g/m² to 5 g/m² of polyhexanide.

TABLE 5

Finishing a tempered nonwoven polyhexanide using a padding machine (Smartcoater, Coatema company)

| | |
|---|---|
| polyhexanide concentration in ethanol [% by weight] | 0.4 |
| speed of the nonwoven | 0.1 m/min |
| length of dryer | 3 m |
| temperature of dryer [° C.] | 70° C. |
| polyhexanide content in the nonwoven | 3.05/m² |

Example 9

Providing the Nonwovens with an Antimicrobial Finish from an Aqueous Solution

A needle-bonded nonwoven is made of water-soluble polyvinyl alcohol staple fibers. The polyvinyl alcohol fibers are water-soluble at a temperature below 25° C. and have a fiber titer of 2.2 dtex at a fiber-staple length of 51 mm. The polyvinyl alcohol fibers are laid by means of a stripper to form a nonwoven and subsequently needle-punched at a penetration density of 100 to 170 penetrations per square centimeter. The needle-bonded polyvinyl alcohol nonwovens are tempered at 150° C. in order to achieve a stabilization of the polyvinyl alcohol. The nonwovens are tempered here in a commercially available laboratory drying cabinet with air circulation over a period of time of 2.5 to 5 hours. After the tempering, the nonwovens are provided with a polyhexanide finish by impregnating them with an aqueous polyhexanide solution. A 20% solution of polyhexanide in distilled water is prepared for this purpose. For example, a coating system having a kiss coater made by the Coatema company (Basecoater or Smartcoater) is employed for this purpose. The kiss coater passes through a bath that is filled with a 20% solution of polyhexanide, then picks up some of the solution and uses it to coat the nonwoven, which is running over the kiss coater. Subsequently, the nonwoven passes through a dryer at a temperature of 70° C. in order to dry the nonwoven. After having been finished with the polyhexanide solution, the nonwoven contains 1 g/m² to 5 g/m² of polyhexanide.

TABLE 6

Finishing a tempered nonwoven with polyhexanide using a kiss coater (Smartcoater, Coatema company)

| | |
|---|---|
| polyhexanide concentration in ethanol [% by weight] | 15 to 20 |
| speed of the nonwoven | 1 m/min |
| length of dryer | 3 m |
| temperature of dryer [° C.] | 70° C. |
| speed of the kiss coater roller | 1 m/min |
| polyhexanide content in the nonwoven | 1 g/m² to 5 g/m² |

Example 10

Determination of the Thermodesorption

Dimethyl sulfoxide and fatty-alcohol ethoxylates, for example, from the brighteners, can be identified in the untempered PVA fibers by means of thermodesorption. After the tempering, the tempered PVA fibers are likewise examined by means of thermodesorption. After the tempering, neither dimethyl sulfoxide nor fatty-alcohol ethoxylates can be detected, so that their content falls below the applicable detection limits.

Consequently, the tempering makes it possible to remove impurities such as, for instance, spinning auxiliaries, solvents or brighteners contained in the nonwoven or in the fibers.

Example 11

XPS Determinations of Tempered and Untempered Nonwovens

A needle-bonded nonwoven is made of water-soluble polyvinyl alcohol staple fibers. The polyvinyl alcohol fibers are water-soluble at a temperature below 25° C. and have a fiber titer of 2.2 dtex at a fiber-staple length of 51 mm. The polyvinyl alcohol fibers are laid by means of a stripper to form a nonwoven and subsequently needle-punched at a penetration density of 100 to 170 penetrations per square centimeter. The needle-bonded polyvinyl alcohol nonwovens are tempered at 150° C. in order to achieve a stabilization of the polyvinyl alcohol. XPS is employed to examine untempered and tempered nonwovens (by means of XPS after various tempering times at 150° C.).

TABLE 7

XPS overview spectrum

|  | untempered nonwoven | nonwoven after a tempering time of 2 to 3 hours at 150° C. | nonwoven after a tempering time of 4 to 5 hours at 150° C. |
| --- | --- | --- | --- |
| C 1s [atom-%] | 81.6 | 84.1 | 84.8 |
| O 1s [atom-%] | 17.8 | 15.9 | 15.2 |
| P 2p [atom-%] | 0.6 | — | — |

It can be seen in the XPS overview spectrum that the intensity of the O 1s decreases. This can be caused by a drop in the residual water (residual moisture) brought about by the tempering.

TABLE 8

High-resolution C 1s spectrum

| Signal | untempered nonwoven | nonwoven after a tempering time of 2 to 3 hours at 150° C. | nonwoven after a tempering time of 4 to 5 hours at 150° C. |
| --- | --- | --- | --- |
| C—C, C—H [area-%] | 74.4 | 84.3 | 86.2 |
| C—OH [area-%] | 23.9 | 10.3 | 5.7 |
| C=O [area-%] | — | 4.0 | 5.5 |
| O—C=O [area-%] | 1.6 | 1.5 | 2.7 |

The following can be seen in the high-resolution C1s spectrum: as the tempering duration of the nonwoven increases, the content of hydroxyl groups in the nonwoven decreases. At the same time, the content of carbonyl groups in the nonwoven increases significantly. The content of carboxy groups also increases. The tempering probably also creates C—O—C cross-links. The XPS examinations show that the tempering causes the nonwovens made of water-soluble polyvinyl alcohol fibers to undergo a change in their chemical structure, as a result of which they exhibit a high stability vis-à-vis aqueous solutions.

The invention claimed is:

1. A plurality of fibers, configured to be hydrogelling, produced from fibers made of a first fiber raw material comprising water-soluble polyvinyl alcohol, polyvinyl alcohol copolymer, or water-soluble polyvinyl alcohol and polyvinyl alcohol copolymer,
    wherein a hydrogelling configuration of the plurality is achieved by
    (i) tempering a fiber raw material at a predetermined tempering temperature that is higher than a glass transition temperature,
        lower than a melting or decomposition temperature, or
        higher than the glass transition temperature and lower than the melting or decomposition temperature of the first fiber raw material, and
    (ii) tempering for a predetermined tempering duration,
    wherein the fiber raw material is cross-linked by the tempering, and
    wherein the plurality has an absorption capacity of 4 to 30 g/g for water, aqueous solutions, or water and aqueous solutions.

2. The plurality of claim 1, wherein the first fiber raw material is a polymer blend further comprising a polyolefin, a polyamide, a polyester, a polyacrylonitrile, a polyvinyl chloride, an elastane, a polyesteramide, a polyvinyl amine, a polyvinyl acetate, a polyethylene glycol, a polyethylene oxide, a polyvinyl pyrrolidone, a polyurethane, a polyacrylate, cellulose, a cellulose derivative, a regenerated cellulose, an alginate, a chitosan, a gelatin, a collagen, a starch, a hyaluronic acid, a pectin, agar, or a mixture thereof.

3. The plurality of claim 1, further comprising:
    additional fibers made of a second fiber raw material comprising a non-gelling fiber raw material, a gelling fiber raw material, or a mixture thereof
    wherein the non-gelling fiber raw material comprises a polyolefin, a cellulose, a cellulose derivative, a regenerated cellulose, a polyamide, a polyacrylonitrile, an elastane, a polyvinyl chloride, an animal natural fiber, a plant-based natural fiber, a polyester, or a mixture thereof,
    wherein the gelling fiber raw material comprises an alginate, a cellulose ether, a cellulose ester, an oxidized cellulose, a bacterial cellulose, a cellulose carbonate, a gelatin, a collagen, a starch, a hyaluronic acid, a pectin, agar, a polyvinyl amine, a polyvinyl acetate, a polyethylene glycol, a polyethylene oxide, a polyvinyl pyrrolidone, a polyurethane, a polyacrylate, or a mixture thereof.

4. The plurality of claim 3, wherein the additional fibers are bi-component fibers, multi-component fibers, polymer blend fibers, or a mixture thereof.

5. The plurality of claim 3, wherein a content of the additional fibers is 10% to 50% by weight.

6. The plurality of claim 1, having a maximum breaking force of 0.3 N/2 cm to 50 N/2 cm in a hydrogelled state.

7. The plurality of claim 1, having a retention capacity of more than 70% for water and/or for aqueous solutions.

8. The plurality of claim 1, having a shrinkage of a given fibrous structure of at most 60% in water, aqueous solutions, or water and aqueous solutions.

9. A method for producing fibers or fibrous structures configured to be hydrogelling, the method comprising:
    tempering fibers or fibrous structures made of a first water-soluble fiber raw material comprising water-soluble polyvinyl alcohol, water-soluble polyvinyl alcohol copolymer, or water-soluble polyvinyl alcohol and water-soluble polyvinyl alcohol copolymer at a predetermined tempering temperature that is
   higher than a glass transition temperature,
   lower than a melting temperature, or
   higher than the glass transition temperature and lower than the melting temperature of the first fiber raw material,
for a predetermined duration, thereby cross-linking the fibers,
   wherein the plurality has an absorption capacity of 4 to 30 g/g for water, aqueous solutions, or water and aqueous solutions.

10. The method of claim 9, wherein the predetermined duration of the tempering ranges from 10 minutes to 14 hours.

11. The method of claim 9, further comprising:
   bonding the fibers to produce a one-dimensional, two-dimensional, or three-dimensional fibrous structure.

12. The method of claim 9, further comprising:
   admixing additional fibers made of at least one second fiber raw material to the fibers.

13. A material for medical application, wound dressing, wound bandage, stitching material, implant, tissue engineering scaffold, drug, support material, insulating material, filter material, technical absorber product, food sector product, hygiene product, cosmetic product, household product, comprising the plurality of claim 1.

14. A wound bandage or wound dressing, comprising the plurality of claim 1.

15. The plurality of claim 1, wherein the first raw material further comprises a polycaprolactone, a polyhexamethylene terephthalate, a polyhydroxybutyrate, a polyhydroxyvalerate, a polyvinyl amine, a polyvinyl acetate, a polyethylene glycol, a carboxymethyl cellulose, a methyl cellulose, a ethyl cellulose, a hydroxymethyl cellulose, a hydroxyethyl cellulose, a hydroxyalkylmethyl cellulose, a hydroxypropyl cellulose, cellulose acetate, or a mixture thereof.

16. The plurality of claim 1, wherein the first raw material further comprises a viscose, a cellulose ether, cellulose ester, an oxidized cellulose, a bacterial cellulose, a cellulose carbonate, or mixture thereof.

17. The plurality of claim 1, having an absorption capacity of 4 to 30 g/g for a 0.9% aqueous solution of sodium chloride or for the Test Solution A according to DIN 13726-1 under Point 3.2.2.3.

18. The plurality of claim 1, wherein the predetermined tempering temperature is higher than the glass transition temperature of the first fiber raw material.

19. The plurality of claim 1, wherein the predetermined tempering temperature is lower than the melting or decomposition temperature of the first fiber raw material.

20. The plurality of claim 1, wherein the predetermined tempering temperature is higher than the glass transition temperature and lower than the melting or decomposition temperature of the first fiber raw material.

* * * * *